US00PP34575P3

(12) United States Plant Patent
Schoone

(10) Patent No.: US PP34,575 P3
(45) Date of Patent: Sep. 13, 2022

(54) ***PHALAENOPSIS* PLANT NAMED 'GRAND MASTER'**

(50) Latin Name: *Phalaenopsis hybrida*
Varietal Denomination: Grand Master

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 17/666,191

(22) Filed: Feb. 7, 2022

(65) Prior Publication Data

US 2022/0256757 P1 Aug. 11, 2022

Related U.S. Application Data

(60) Provisional application No. 63/147,984, filed on Feb. 10, 2021.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Phalaenopsis* plant named 'Grand Master', characterized by its upright plant habit; moderately vigorous growth habit; strong flowering stems; strong and moderately elongated leaves; freely flowering habit with typically two inflorescences per plant, each inflorescence with numerous flowers; dark purplish red-colored flowers with white, violet and yellow-colored labellum; and good postproduction longevity.

2 Drawing Sheets

Figure 1:
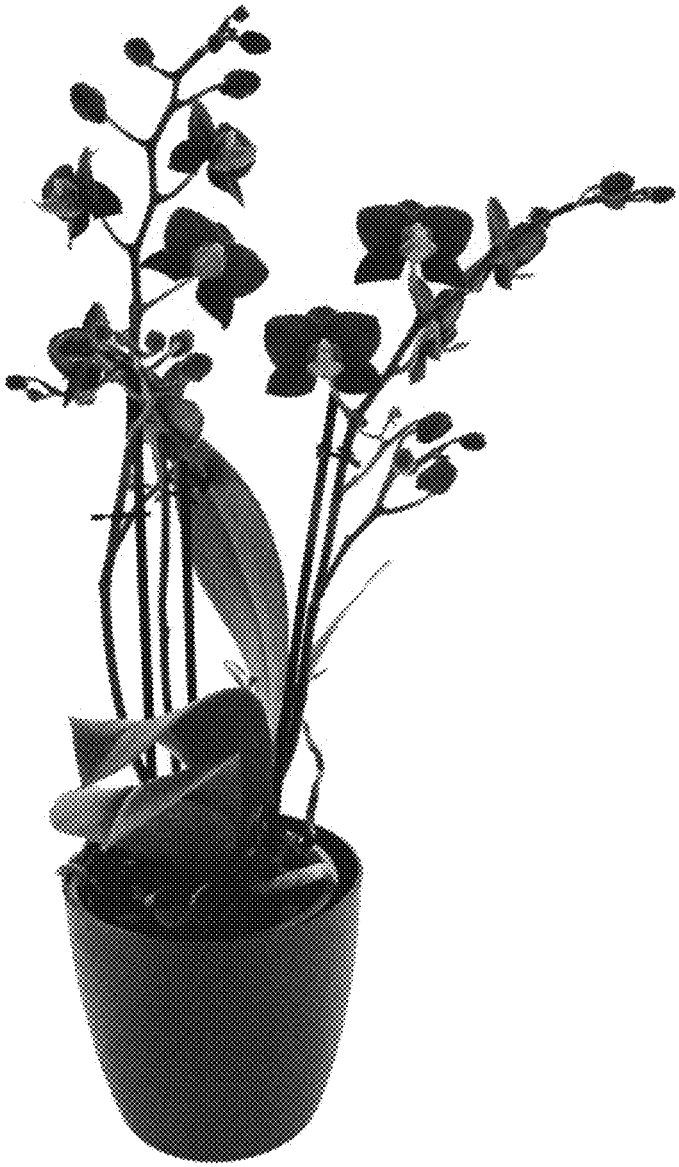

Botanical designation: *Phalaenopsis hybrida.*
Cultivar denomination: 'GRAND MASTER'.

STATEMENT REGARDING PRIOR DISCLOSURES BY INVENTOR and APPLICANT/ASSIGNEE

An European Community Plant Breeder's Rights application for the instant plant was filed by the Applicant/Assignee of the instant application, Floricultura B.V. of Heemskerk, The Netherlands on Oct. 1, 2021, application number 2021/2426. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Grand Master'.

The new *Phalaenopsis* plant is a product of a planned breeding program conducted by the Inventor in Nantou, Taiwan and Heemskerk, The Netherlands. The objective of the breeding program is to develop new fast-growing and freely flowering *Phalaenopsis* plants with good leaf shape and large flowers with unique and attractive patterns and coloration.

The new *Phalaenopsis* plant originated from a cross-pollination on Jun. 13, 2014 in Nantou, Taiwan of a proprietary breeding selection identified as *Phalaenopsis hybrida* 'Sunrise Red Peoker' X 'Sogo Lisa', not patented, as the female, or seed, parent with *Phalaenopsis hybrida* 'Yu Pin Burgundy', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in June, 2018.

Asexual reproduction of the new *Phalaenopsis* plant by in vitro meristem propagation in a controlled environment in Assendelft, The Netherlands since June, 2019 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Grand Master'. These characteristics in combination distinguish 'Grand Master' as a new and distinct *Phalaenopsis* plant:

1. Upright plant habit.
2. Moderately vigorous growth habit.
3. Strong flowering stems.
4. Strong and moderately elongated leaves.
5. Freely flowering habit with typically two inflorescences per plant, each inflorescence with numerous flowers.
6. Dark purplish red-colored flowers with white, violet and yellow-colored labellum.
7. Good postproduction longevity.

Plants of the new *Phalaenopsis* can be compared to plants of the female parent selection. Plants of the new *Phalaenopsis* differ primarily from plants of the female parent selection in flower color as plants of the new *Phalaenopsis* have dark purplish red-colored flowers whereas plants of the female parent selection have yellow-colored flowers with numerous stripes.

Plants of the new *Phalaenopsis* can be compared to plants of the male parent, 'Yu Pin Burgundy'. Plants of the new *Phalaenopsis* differ primarily from plants of 'Yu Pin Burgundy' in flower color as plants of the new *Phalaenopsis* have dark purplish red-colored flowers with white, violet and yellow-colored labellum whereas plants of 'Yu Pin Burgundy' have burgundy-colored flowers purplish red and cream-colored labellum and numerous spots.

Plants of the new *Phalaenopsis* can be compared to plants of *Phalaenopsis hybrida* 'Scarlet Jubilee', not patented. In side-by-side comparisons, plants of the new *Phalaenopsis* differ primarily from plants of 'Scarlet Jubilee' in plant size as plants of the new *Phalaenopsis* are shorter than plants of 'Scarlet Jubilee'. In addition, petals of plants of the new *Phalaenopsis* have narrow white-colored edges whereas petals of plants of 'Scarlet Jubilee' do not have colored edges.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Grand Master' grown in a container.

Figure 2:
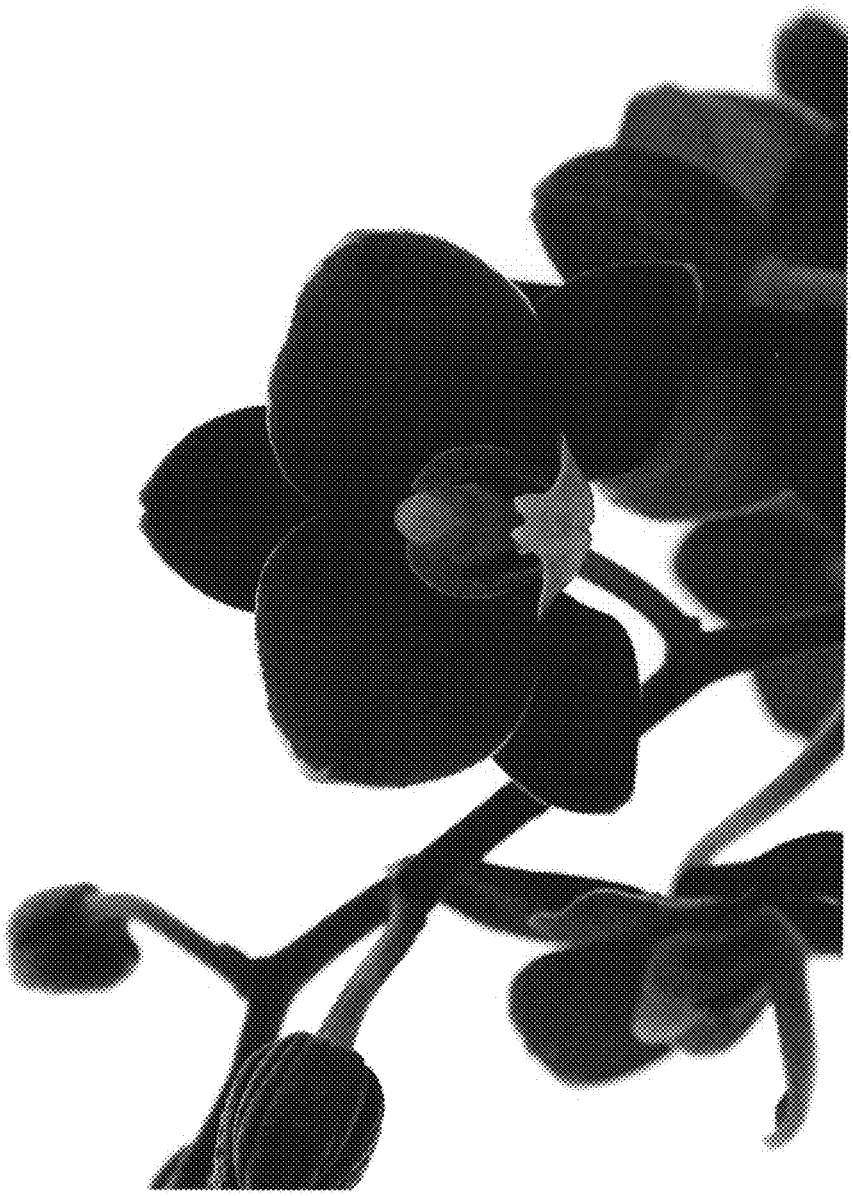

The photograph on the second sheet (FIG. 2) is a close-up view of typical flowers of 'Grand Master'.

DETAILED BOTANICAL DESCRIPTION

The aforementioned photographs and following observations and measurements describe plants grown during the autumn in 10.5-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the production of the plants, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Grand Master'.

Parentage:

*Female parent*.—Proprietary breeding selection identified as *Phalaenopsis hybrida* 'Sunrise Red Peoker' X 'Sogo Lisa', not patented.

*Male parent*.—*Phalaenopsis hybrida* 'Yu Pin Burgundy', not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thin, fibrous; typically light yellowish white in color; actual color of the roots is dependent on substrate composition, water quality, fertilizer, substrate temperature and age of roots.

*Rooting habit*.—Freely branching; medium density.

Plant description:

*Plant form and growth habit*.—Herbaceous epiphyte; upright plant habit with typically two inflorescences per plant, each inflorescence with numerous flowers; monopodial; moderately vigorous growth habit and moderate growth rate.

*Plant height, substrate level to top of foliar plane*.—About 15.2 cm.

*Plant height, substrate level to top of inflorescences*.—About 34.4 cm.

*Plant diameter or spread*.—About 24.1 cm.

Leaf description:

*Arrangement and quantity*.—Distichous, simple; sessile; about five leaves per plant.

*Length*.—About 17.5 cm.

*Width*.—About 7.1 cm.

*Aspect*.—Uptight to outwardly arching.

*Shape*.—Oblong to narrowly obovate; slightly carinate.

*Apex*.—Unequal obtuse.

*Base*.—Sheathing. Sheath length: About 1.4 cm. Sheath width: About 1.2 cm. Sheath color: Close to 143A.

*Margin*.—Entire; not undulate.

*Texture and luster, upper and lower surfaces*.—Smooth, glabrous; slightly glossy.

*Venation pattern*.—Camptodromous.

*Color*.—Developing leaves, upper surface: Close to NN137B. Developing leaves, lower surface: Close to 146A and 146B; towards the margins, tinged with close to 147A. Fully expanded leaves, upper surface: Close to NN137B; venation, close to 137A. Fully expanded leaves, lower surface: Close to 146A; venation, close to NN137A.

Inflorescence description:

*Appearance and flowering habit*.—Showy zygomorphic flowers arranged on axillary branched racemes; typically two inflorescences per plant; each inflorescence with about 18 flowers; flowers face outwardly on arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about eight weeks on the plant; flowers not persistent.

*Inflorescence length* (*lowermost flower to inflorescence apex*).—About 25 cm.

*Inflorescence width*.—About 17.1 cm.

*Flower buds*.—Height: About 1.7 cm. Diameter: About 1.2 cm by 1.4 cm. Shape: Broadly ovate. Color: Close to 148A; venation, close to 177A; at the margins of the immature sepals, close to N186C.

*Flower size*.—About 4.6 cm (vertical) by 4.4 cm (horizontal).

*Flower depth*.—About 3.2 cm.

*Petals, quantity and arrangement*.—Three, two lateral petals and one center petal transformed into a labellum.

*Lateral petals*.—Length: About 2.3 cm. Width: About 2.3 cm. Shape: Broadly ovate to roughly deltoid; very slightly convex. Apex: Obtuse to broadly and bluntly acute. Margin: Entire. Texture and luster, upper surface: Smooth, glabrous, velvety; matte. Texture and luster, lower surface: Smooth, glabrous, slightly velvety; matte. Color: When opening, upper surface: Close to N186C; center, tinged with a blend of 53A and N186C; narrow margin edges, close to 157A to 157D. When opening, lower surface: Close to a blend of 85D, N187D and 201D; towards the margins and apex, close to N79B; and narrow margin edges, close to 157A to 157D. Fully opened, upper surface: Close to 187B; towards the margins and apex, close to 187A; narrow margin edges, close to 155A; color does not change with subsequent development. Fully opened, lower surface: Close to 84C; towards the margins and apex, close to N79C; narrow margin edges, close to 155A; color does not change with subsequent development.

*Labella*.—Appearance: Three-parted with two lateral lobes and a central lobe. Length, lateral lobes: About 1.2 cm. Width, lateral lobes: About 7 mm. Length, central lobe: About 1.7 cm. Width, central lobe: About 2.5 mm to 15 mm. Shape, lateral lobes: Obovate. Shape, central lobe: Ovate. Apex, lateral lobes: Obtuse. Apex, central lobe: Emarginate. Margins, lateral and central lobes: Entire. Texture and luster, upper and lower surfaces: Smooth, glabrous, moderately velvety; matte. Callosities: Located at the base of the labellum and attachment point of the lateral petals; about 3 mm in length, about 2 mm in width and about 2 mm in height. Color: When opening, upper surface: Lateral lobes: Darker than N79A; basal margin, close to N155C; apical margin, close to 76C; heavily mottled and densely dotted with close to a blend of N78B and NN78B. Central lobe: Close to N78C; towards the apex, close to NN155B; below the callosities, tinged with close to 17D; heavily marbled and flushed with close to 64A and 64B; and at the base, close to 76A. Callosities: Slightly darker than N77A. When opening, lower surface: Lateral lobes: Close to blend of 79A and N79A; basal and apical margins, close to 84D; heavily mottled and densely dotted, close to N78A and N78B. Central lobe: Close to 76A; towards the apex, close to 76C; margins, close to 64A and 64B; at the base, close to 187C and 187D; dots, close to N78A to NN78A and NN78B. Fully opened, upper surface: Lateral lobes: Darker than N79A; basal margin, close to 158D; apical margin, close to 76C; heavily mottled and densely dotted with close to a blend of N78A and NN78A. Central lobe: Close to N78C; towards the apex, close to NN155C to NN155D; below the callosities, slightly tinged with close to 20B; heavily marbled and flushed with close to 71A and 72A; and at the base, close to 76A. Callosities: Close to N77A. Fully opened, lower surface: Lateral lobes: Close to blend of 79A and N79A; basal and apical margins, close to 84D; heavily mottled and densely dotted, close to a blend of N78A and N78B. Central lobe: Close to 76A; towards the apex, close to 76C; margins, close to 64A and 64B; at the base, close to 187C and 187D; dots, close to N78A to NN78A and NN78B.

*Sepals*.—Quantity and arrangement: Three, one upper dorsal sepal and two lower lateral sepals. Length, dorsal and lateral sepals: About 2.55 cm. Width, dorsal and lateral sepals: About 1.7 cm. Shape, dorsal sepal: Broadly elliptic to slightly obovate. Shape, lateral sepals: Ovate. Apex, dorsal sepal: Bluntly acute. Apex, lateral sepals: Acute to bluntly acute. Base, dorsal and lateral sepals: Truncate. Margin, dorsal and lateral sepals: Entire. Texture and luster, dorsal and lateral sepals, upper surface: Smooth, glabrous, moderately velvety; matte. Texture and luster, dorsal and lateral sepals, lower surface: Smooth, glabrous, moderately bullate; matte. Color, dorsal sepal: When opening, upper surface: Close to N186C; narrow margin edges, close to 155A. When opening, lower surface: Close to 197B; margins, close to N186C. Fully opened, upper surface: Close to a blend of N186C and 187A; narrow margin edges, close to N155C. Fully opened, lower surface: Close to N77D; towards the margins and apex, close to 187A. Color, lateral sepals: When opening, upper surface: Close to a blend of N186C and 200A; narrow margin edges, close to N155C. When opening, lower surface: Close to 197B; margins, close to N186C. Fully opened, upper surface: Close to a blend of N186C and 187A; narrow margin edges, close to N155C. Fully opened, lower surface: Close to N77B; towards the margins and apex, close to 187A.

*Peduncles*.—Length: About 36.4 cm. Diameter: About 5 mm. Strength: Strong. Aspect: Upright to outwardly arching. Texture and luster: Smooth, glabrous; matte. Color: Close to 146B; moderately covered with fine dots and stripes, close to 145A.

*Pedicels*.—Length: About 3.1 cm. Diameter: About 2.5 mm. Strength: Moderately strong. Aspect: About 50° from peduncle axis. Texture and luster: Smooth, glabrous; matte. Color: Close to lighter than 147D; proximally, strongly tinged with close to N77B.

*Reproductive organs*.—Androecium: Column length: About 8.5 mm. Column width: About 5 mm. Column color: Close to 76C; central band, close to N78C. Pollinia quantity: Two. Pollinia diameter (per two pollinia): About 2.25 mm. Pollinia color: Close to 17A. Gynoecium: Stigma length: About 3.5 mm.

Stigma width: About 4 mm. Stigma shape: Reniform. Stigma color: Close to N155A. Ovary length: About 9 mm. Ovary diameter: About 1 mm. Ovary color: Close to 145A. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Grand Master' as illustrated and described.

* * * * *